(12) United States Patent  
Shimizu et al.

(10) Patent No.: US 7,632,366 B2
(45) Date of Patent: Dec. 15, 2009

(54) FOLDING MACHINE AND PROCESS FOR PRODUCING ARTICLE BEING FIXED

(75) Inventors: Masaru Shimizu, Osaka (JP); Kazuo Okubo, Osaka (JP); Kikuo Yoneoka, Osaka (JP)

(73) Assignee: Zuiko Corporation, Osaka (JP)

( * ) Notice: Subject to any disclaimer, the term of this patent is extended or adjusted under 35 U.S.C. 154(b) by 875 days.

(21) Appl. No.: 10/549,470

(22) PCT Filed: Mar. 19, 2004

(86) PCT No.: PCT/JP2004/003800

§ 371 (c)(1),
(2), (4) Date: Sep. 14, 2005

(87) PCT Pub. No.: WO2004/085300

PCT Pub. Date: Oct. 7, 2004

(65) Prior Publication Data

US 2006/0196594 A1    Sep. 7, 2006

(30) Foreign Application Priority Data

Mar. 27, 2003    (JP) .............................. 2003-087427

(51) Int. Cl.
*B32B 41/00*    (2006.01)
(52) U.S. Cl. .......................... 156/64; 156/361; 156/378; 156/379
(58) Field of Classification Search .................. 156/64, 156/163, 164, 196, 199, 204, 217, 227, 250, 156/256, 361, 378, 379, 438, 443, 459, 494, 156/496; 112/147, 470.16, 475.06

See application file for complete search history.

(56) References Cited

U.S. PATENT DOCUMENTS 1,865,945 A    7/1932    Monforts et al.

(Continued)

FOREIGN PATENT DOCUMENTS

| DE | 1 944 633 | 3/1971 |
| DE | 25 03 701 | 8/1976 |
| EP | 1 270 480 A2 | 1/2003 |
| EP | 1 362 815 A2 | 11/2003 |

(Continued)

OTHER PUBLICATIONS

European Patent Office Communication for corresponding Application No. 04 722 079.3 dated Dec. 17, 2007.
International Search Report for corresponding Application No. PCT/JP2004/003800, mailed Apr. 20, 2004.

*Primary Examiner*—George R Koch, III
(74) *Attorney, Agent, or Firm*—Renner, Otto, Boisselle & Sklar, LLP

(57) ABSTRACT

A folding apparatus of the present invention comprises a folding section 40 for folding a web W in two so that opposite side edges W1, W2 of the web W are in a predetermined positional relationship with respect to each other; a correction section 90 for correcting a moving direction of the web W by contacting the web W in the folding section 40; a detecting section 41, 103 for detecting a reference portion W1, W2 of the web to be used as a reference in a web folding operation so as to output positional information regarding a position of the detected reference portion W1, W2; and a control section 3 for controlling the correction section 90 based on the positional information so as to change a state of contact of the contact of the correction section 90 with the web W.

10 Claims, 5 Drawing Sheets

U.S. PATENT DOCUMENTS

| | | | |
|---|---|---|---|
| 2,619,057 A | 11/1952 | Ellis, Sr. |
| 2,900,934 A | 8/1959 | Judelson |
| 3,013,513 A | 12/1961 | Judelson |
| 3,745,947 A | 7/1973 | Brocklehurst |
| 3,759,198 A | 9/1973 | Pisani |
| 3,828,367 A | 8/1974 | Bourgeois |
| 5,711,832 A | 1/1998 | Glaug et al. |
| 6,546,987 B1 | 4/2003 | Tachibana et al. |
| 6,722,494 B2 | 4/2004 | Nakakado |
| 6,913,664 B2 | 7/2005 | Umebayashi et al. |
| 7,097,725 B2 * | 8/2006 | Yoneoka et al. | 156/161 |
| 2002/0174930 A1 | 11/2002 | Umebayashi et al. |

FOREIGN PATENT DOCUMENTS

| | | |
|---|---|---|
| JP | 62-32838 | 8/1987 |
| JP | 04-197963 A | 7/1992 |
| JP | 2000-255518 | 9/2000 |
| JP | 2003-038566 | 2/2003 |
| JP | 2004-043179 A | 2/2004 |
| WO | 01/44086 A1 | 6/2001 |

* cited by examiner

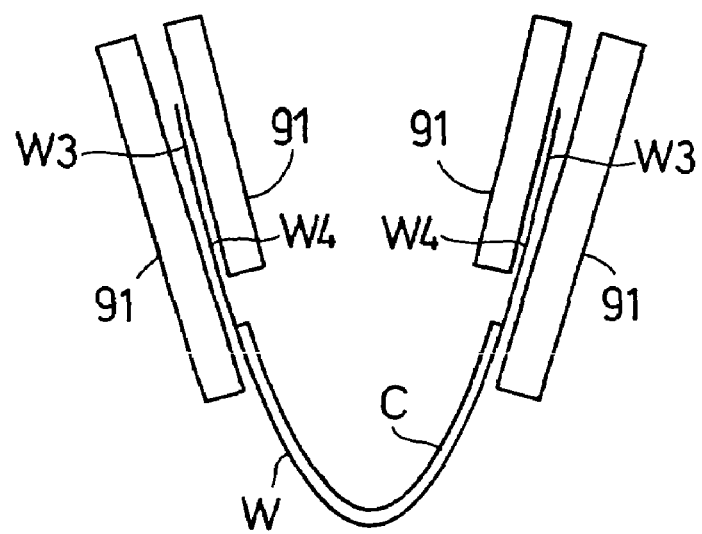
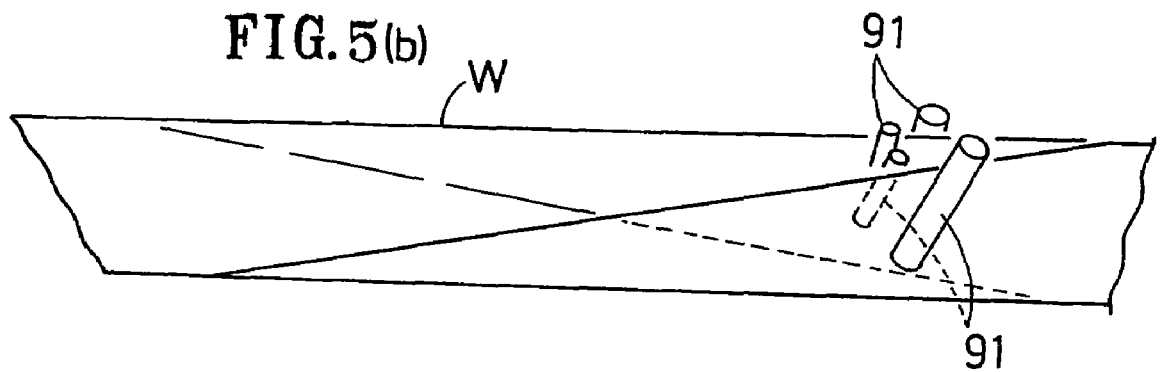

FOLDING MACHINE AND PROCESS FOR PRODUCING ARTICLE BEING FIXED

This application is a national stage entry of PCT/JP04/03800, filed Mar. 19, 2004.

TECHNICAL FIELD

The present invention relates to a web folding apparatus and a method for producing a worn article.

BACKGROUND ART

During the process of producing a worn article, a semi-finished product thereof, e.g., a web, is sometimes folded in two (for example, U.S. Pat. No. 3,828,367). When a web is folded in two, it is ideally folded with the edges on both sides being aligned with each other. However, it is typically difficult to fold a web in such a manner.

It is therefore an object of the present invention to provide a folding apparatus and a method for producing a worn article in which a web is folded in two, wherein the two edge portions (opposite side edges) of the web can be brought into a predetermined positional relationship.

DISCLOSURE OF THE INVENTION

A folding apparatus of the present invention includes: a folding section for folding in two a web being continuous in a conveyance direction of the web so that opposite side edges of the web are in a predetermined positional relationship with respect to each other; a correction section for correcting the conveyance direction of the web (giving a change to the conveyance direction) by contacting a surface of the web in the folding section; a detecting section for detecting a reference portion of the web to be used as a reference in a web folding operation so as to output positional information regarding a position of the detected reference portion; and a control section for controlling the correction section based on the positional information so as to bring a positional relationship between the opposite side edges of the web closer to the predetermined positional relationship by changing a state of contact of the correction section with the web.

Another folding apparatus of the present invention is a folding apparatus for folding in two a continuous web being continuous in a running direction of the web so that opposite side edges of the web are in a predetermined positional relationship with respect to each other, the apparatus including: an abutting member provided so as to extend in the running direction between the opposite side edges of the web, wherein the abutting member abuts against the web to fold the web into a V or U shape; a nipping member provided downstream of the abutting member for nipping the web folded by the abutting member so as to fold the web in two; a contact section provided between an upstream end of the abutting member and the nipping member for contacting an inner surface and/or an outer surface of the web being folded in the V or U shape; a detecting section for detecting a reference portion of the web to be used as a reference in a web folding operation so as to output positional information regarding a position of the detected reference portion; a driving section for changing a state of contact of the contact section and/or the abutting member with the web; and a control section for controlling an action of the driving section based on the positional information so as to bring a positional relationship between the opposite side edges of the web closer to the predetermined positional relationship.

In the present invention, the reference portion of the web is detected, and the running direction of the web is corrected so as to reduce the diversion of the path of the web. Specifically, the tension acting upon the opposite side edge portions of the web is adjusted by changing the state of contact of the correction section with the web or by changing the state of contact of the contact section or the abutting member. Thus, the path of the web is adjusted, and the positional relationship between the opposite side edges of the web is brought closer to a predetermined positional relationship. Therefore, it is possible to fold the web into a predetermined state.

Particularly, the web guider directly corrects the moving direction of the web by exerting an external force on the web in the folding section, i.e., exerting an external force on a portion of the web that has started to be folded. Therefore, even if the web runs at a high speed, it is possible to fold the web in two so that the opposite side edges of the web are in a predetermined positional relationship with respect to each other.

The method for "changing the state of contact" may be changing the inclination angle of the contact section contacting the web with respect to the running direction of the web, or changing the rotation speed or the rotation resistance of the rollers contacting the web.

By changing the inclination angle, the rotation speed or the rotation resistance, the external force that the web receives from the contact section changes, thereby changing the tension on the opposite side edge portions of the web.

In the present invention, typically, the detecting section generates the positional information by using each of the opposite side edges of the web as a "reference portion". In a case where a graphical pattern or a picture is printed on the web, such a graphical pattern or a picture may alternatively be used as the reference portion, in which case the detecting section generates the positional information of the web by detecting the reference portion and performing an image processing operation.

The detecting section for detecting the reference portion may be an ultrasonic sensor, an optical sensor (e.g., an infrared sensor), an air sensor, etc. Alternatively, the deviation of the web may be detected by processing an image obtained by using a CCD camera or a linear sensor (line sensor).

The type of a sensor is appropriately selected depending on the type of the web. For example, in a case where the air can be easily passed through the web, it is preferred to use an ultrasonic sensor or an optical sensor. In a case where the web is transparent or semitransparent, it is preferred to use an ultrasonic sensor or an air sensor.

In the present invention, the detection of the opposite side edges, as the reference portions, is preferably performed before the web is completely folded in two. It is generally preferred that the detection is performed when the web not folded at all is starting to be folded, or immediately before the web is completely folded in two. More specifically, it is preferred that the detection is performed upstream and/or downstream of the abutting member for folding the web in two in the folding section. However, the position at which the detection of the present invention is performed is not limited to any particular position. Alternatively, even after the web is folded, a deviation (misalignment) between the edges of the folded web may be detected by using a detector having a high precision.

Note that the "folding section" as used herein refers to a section responsible for the process of folding the web so that the opposite side edges of the web are in a predetermined positional relationship with respect to each other, starting from a state where the web is not folded at all. In the present invention, it is preferred that a sensor for detecting at least the side edges is located in the "folding section".

With producing a worn article, the web is typically folded in two so that the positions of the opposite side edges are aligned with each other. However, it is not always necessary that the positions of the opposite side edges are aligned with each other. In the present invention, the web is folded in two while correcting the path of the web so as to "bring the relationship between the opposite side edges closer to a predetermined relationship (a relative positional relationship)". For example, the web may be folded in two so that one of the opposite side edges of the web is protruding past the other side edge by a predetermined amount.

Note that the term "opposite side edges" of a web refers to a pair of side edges thereof that are parallel to the running direction of the web.

In an embodiment of the present invention, the path of the web can be corrected by adjusting the tension acting upon the opposite side edge portions of the web while the web is being carried. Moreover, the abutting member may be controlled based on the positional information to be moved in the width direction and in the vertical direction. However, the present invention does not limit the structure of the mechanism or apparatus for correcting the relative position of the web with respect to the abutting member.

A method for producing a worn article of the present invention includes the steps of: placing an absorbent body on a surface of a web; folding the web in two in a folding section so that opposite side edges of the web are close to or aligned with each other; detecting a reference portion of the web to be used as a reference in a folding operation to generate positional information regarding a position of the detected reference portion; correcting a path of the web based on the positional information so that the opposite side edges of the folded web are in a predetermined positional relationship with respect to each other by a contact section contacting with the web in the folding section; bonding portions of the folded web to each other to form a bonded portion; and cutting the bonded web along the bonded portion.

Note that "worn article" includes a sanitary napkin, and the like, as well as a disposable diaper and disposable pants.

BRIEF DESCRIPTION OF THE DRAWINGS

The present invention will be understood more apparently from the following description of preferred embodiment when taken in conjunction with the accompanying drawings. However, it will be appreciated that the embodiments and the drawings are given for the purpose of mere illustration and explanation and should not be utilized to define the scope of the present invention. The scope of the present invention is to be defined only by the appended claims. In the drawings annexed, the same reference numerals denote the same or corresponding parts throughout several views.

FIGS. 5(*a*) and 5(*b*) are a transverse sectional view and a perspective view, respectively, showing another example of a contact section.

BEST MODE FOR CARRYING OUT THE INVENTION

An embodiment of the present invention will now be described with reference to the drawings.

Figure 1:
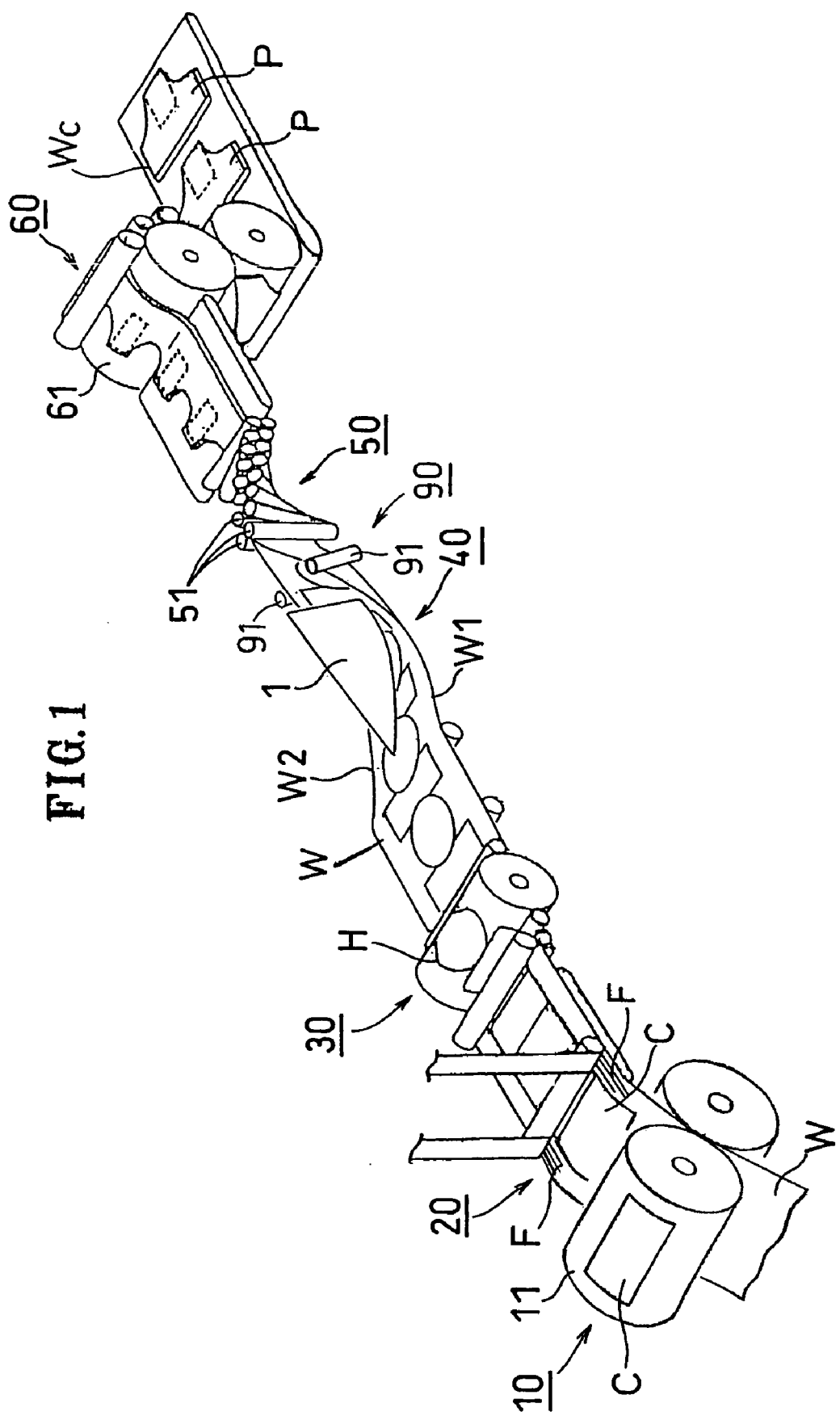
FIG. 1 is a schematic perspective view showing a production apparatus for producing a disposable worn article according to an embodiment of the present invention.

A production apparatus shown in FIG. 1 includes a placement section 10, an attachment section 20, a hole-forming section 30, a folding section 40, a twisting section 50, and a bonding/cutting section 60.

As will be described below, this apparatus continuously carries a web W while performing various processes in the sections 10, 20, ..., 60. In the placement section 10, absorbent bodies C are placed at regular intervals on the web W. For example, the absorbent body C may be placed directly onto the web W by a drum 11, or the like, or the absorbent body C may be first placed on another web, which is then placed over the web W.

In the attachment section 20 of FIG. 1, a waist elastic member F is introduced onto the web W on which the absorbent bodies C are placed. In a case where the absorbent body C is placed on another web 12 of FIG. 2, a waist elastic member F2 may be introduced between the web W and the other web 12 denoted by a broken line.

Figure 2:
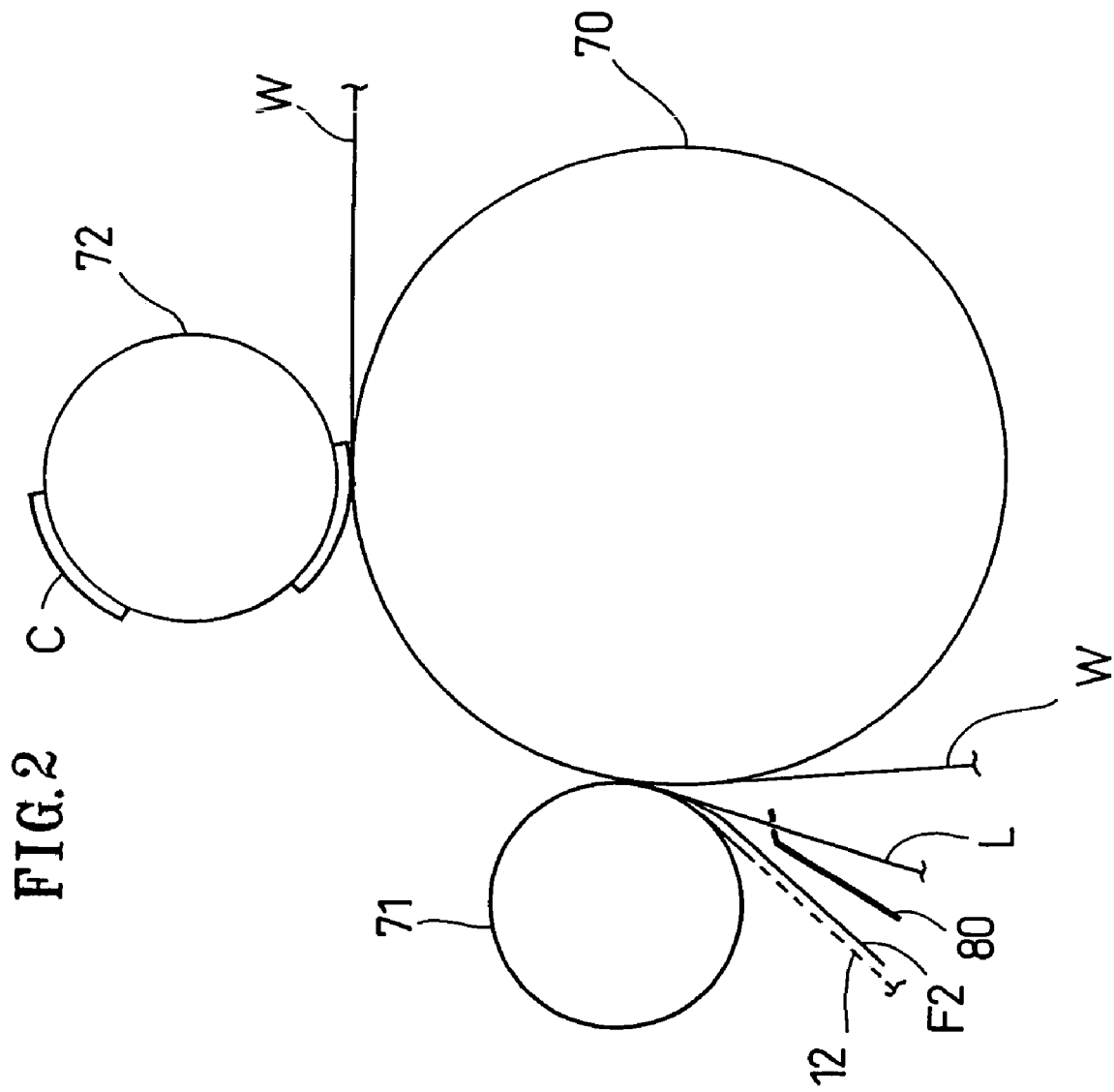
FIG. 2 is a schematic side view showing an attachment section.

Moreover, as shown in FIG. 2, in a case where a leg elastic member L for forming leg gathers is placed on the web W before the absorbent body C is placed on the web W, the leg elastic member L and the waist elastic member F2 may be simultaneously attached onto the web W. For example, the waist elastic member F2 and the leg elastic member L are fixed between the web W and the other web 12 while being passed between nip rollers 70 and 71. The leg elastic member L is introduced between the webs W and 12 by an inserting section 80 moving in the width direction of the web W. The absorbent body C is placed by a drum 72 onto the web W with the other web 12, etc., placed thereon.

Then, the web W with the absorbent body C placed thereon is passed to the hole-forming section 30 of FIG. 1.

In the hole-forming section 30 of FIG. 1, holes H to be leg holes are formed by a leg hole cutter (the anvil roller is not shown) at regular intervals in the web W, onto which the waist elastic member F has been introduced. The cut-off portions are ejected out of the production line by means of vacuum, or the like. Alternatively, the holes H to be leg holes may be formed before the waist elastic member F is introduced or before the absorbent body C is placed.

After the holes H are formed in the web W and the waist elastic member F is placed thereon, the web W is passed to the folding section 40. In the folding section 40, the web W is folded into a approximately V or U shape as shown in FIGS. 4(*a*) to 4(*d*), and then folded in two so that a first side edge W1 and a second side edge W2 of the web W are aligned with each other (so that the positions of the side edges W1 and W2 coincide with each other). In this process, the web may alternatively be folded in two so that one of the opposite side edges of the web is protruding past the other side edge by a predetermined amount.

The folding section 40 of FIG. 1 includes a folding sailor (the abutting member) 1. The bottom portion of the folding sailor 1 is in contact with the approximately central portion of the web W in the width direction thereof, and the web is folded in two so that the first side edge W1 and the second side edge W2 of the web W are aligned with each other (so that the positions of the side edges W1 and W2 coincide with each other). The folding sailor 1 may have a three-dimensional shape such as a boat shape or may be formed by frames that together form a predetermined shape. Note that the details of the folding section 40 will be described later.

After the web W is folded in two by the sailor 1, the web W is nipped (sandwiched) between a plurality of guide bars (an example of the nipping member) 51 so as to be completely folded in two, while the web W is twisted by approximately 90° by the 90°-twisting section 50 including a plurality of the guide bars 51. The twisting section 50 may be a twisting section as described in Japanese Patent Laid-Open No. 2003-38566, for example.

The web W being twisted by the twisting section 50 is sealed (bonded) on a drum 61 of the bonding/cutting section 60. The web W may be sealed by, for example, a heat sealing method as shown in Japanese Patent Laid-Open No. 2000-255518 or by an ultrasonic sealing method. A bonded portion Wc formed by the seal partitions adjacent diapers P and P from each other. The bonded portion Wc of the web formed by the seal is cut by a cutter (not shown), whereby the diaper P is separated from the web W.

Note that, as necessary, the orientation (direction) of the diaper P may be turned by about 90°, and the interval between the adjacent diapers P and P may be altered. For example, the diaper P may be placed on a pad moving on a drum, and the orientation (direction) of the pad may be rotated by about 90° or the speed thereof may be changed, thereby altering the orientation (direction) of the diaper P or the interval between the diapers P and P. An example of such an apparatus is disclosed in International Publication WO 01/044086, etc.

Next, the details of an example of the folding section 40 will be described with reference to FIG. 3.

The folding section 40 includes the folding sailor (an example of the correction section and an example of the abutting member) 1 for folding the web W in two, a first sensor (an example of the detecting section) 41 for detecting a positional misalignment (displacement) of the web W, a control section 3 receiving a signal from the first sensor 41, and a web guider 90.

The first sensor 41 detects the side edges (reference portions) W1 and W2 of the web W, which are used as a reference in the operation of folding the web W in two, and generates positional information indicating whether the web W is deviating toward the side edge W1 or the side edge W2 and the amount of deviation. For example, the first sensor 41 is provided in the folding section 40, and generates the positional information of the side edges W1 and W2 before the web W is completely folded.

It is preferred that the first sensor 41 is provided downstream of the web guider 90. Such an arrangement allows for confirmation of the correction made by the web guider 90.

It is preferred that the first sensor 41 is provided in a position where it can detect the positional information of the side edges W1 and W2 of the web W before the web W is completely folded. Detecting a deviation of the side edges W1 and W2 of the web W before the web W is completely folded gives an advantage that an expensive sensor is not needed. Note that it is also possible to detect a deviation of the web W by processing an image after the web W is completely folded.

A pair of first sensors 41 may be provided.

In a case where a pair of first sensors 41 are provided, the control section 3 may correct the path of the web W as follows. First, the value of positional information from one of the first sensors 41 is subtracted from the value of positional information from the other first sensor 41 to obtain a subtraction value. Then, the subtraction value is squared to obtain a calculated value. The path of the web W can be corrected so as to bring the calculated value closer to a target value (e.g., "0"). Such a control provides a better detection accuracy than that in a case where there is only one first sensor 41.

In a case where a pair of first sensors 41 are provided, even if one of the first sensors 41 breaks down, the positional information of the web W can still be obtained by using the other first sensor 41. For example, when the control section 3 detects an abnormality in one of the first sensors 41, the control section 3 generates positional information based on the positional information from the other first sensor 41 that is operating normally. Note that detection of an abnormality in a sensor is disclosed in Japanese Patent Laid-Open No. 2003-38566.

The first sensor 41 and a second sensor 103 to be described later may be a chase-type detector provided with a mechanism for chasing or following the displacement of the side edges W1 and W2 of the web W to calculate the displacement of the side edges W1 and W2 based on the amount of chasing.

The web guider 90 includes a contact section (an example of the correction section) 91 that contact the outer surface and/or the inner surface of the web W, and a driving section 92 for driving the contact section 91. In the embodiment shown in FIG. 4(a), two contact sections 91 are provided on opposite sides of the web W so as to contact an outer surface W3 of the web W. When the contact sections 91 contact the surface W3 and/or W4 of the web W, the tension on the web W changes, thereby changing the path of the web W. It is preferred that the contact section 91 is provided between an upstream end 19 of the folding sailor (the abutting member) 1 and the guide bars (the nipping member) 51. The outer surface W3 of the web W is one surface of the web W on which the absorbent body C is not placed. The inner surface W4 of the web W is another surface of the web W on which the absorbent body C is placed.

Figure 3:
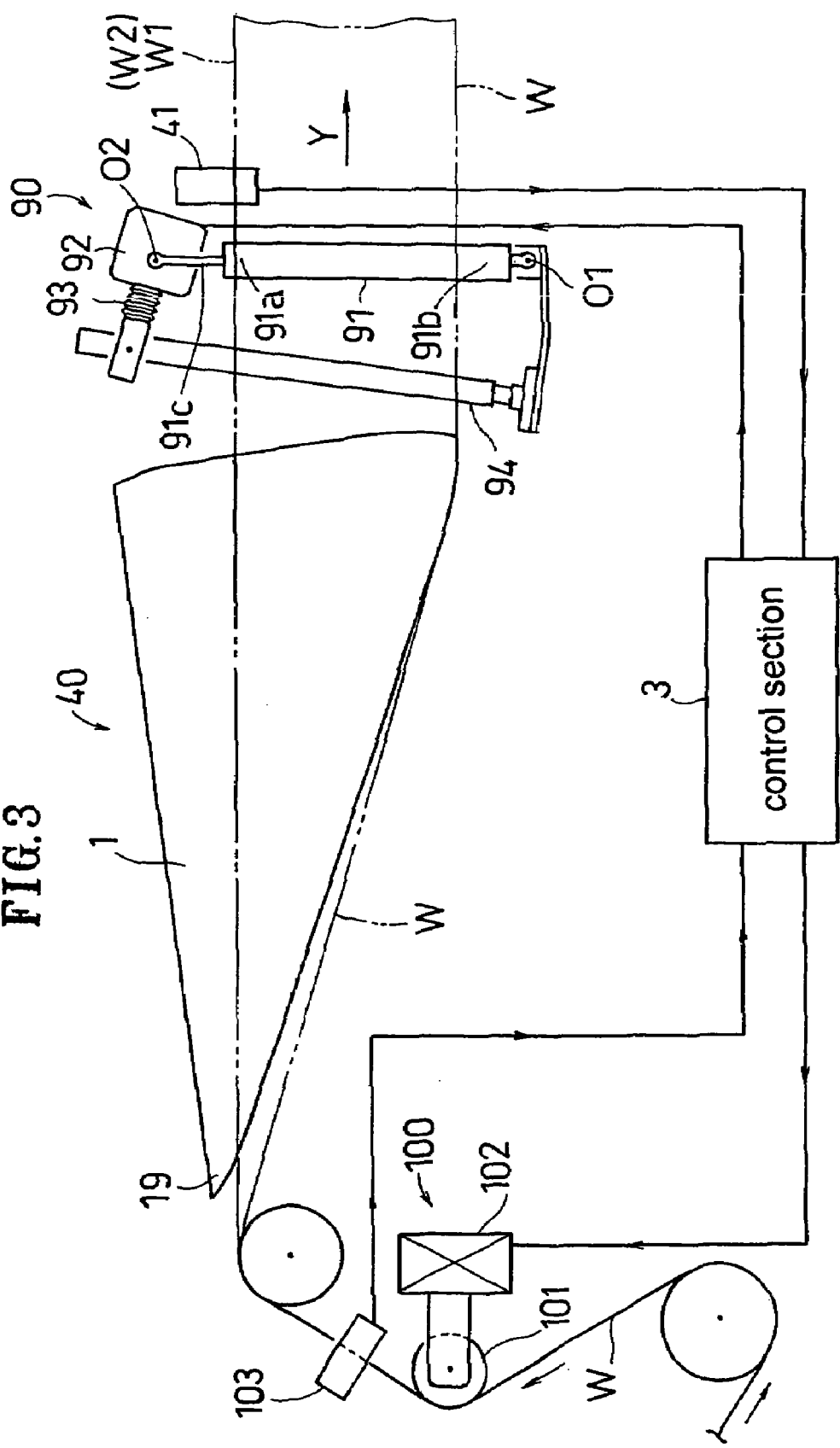
FIG. 3 is a schematic side view showing a folding section.

The change in the path of the web W is detected by the first sensor 41 of FIG. 3 as the positional information of the web W. The control section 3 produces control information so that the positional information is brought to the target value. The driving section 92 receives the control information. Based on the control information, the driving section 92 drives an expansion/contraction section 93 to expand/contract the expansion/contraction section 93, whereby the driving section 92 changes the orientation of the contact section 91. Thus, for example, the positions of the two side edges W1 and W2 of the web W can be aligned with each other.

A compensator may be provided for modeling the web guider 90 system in an autoregressive model or an ARMA model (autoregressive moving average model) based on the positional information and the control information, thus stabilizing the web guider 90 system. Alternatively, the web guider 90 system may be controlled by a neural network or a fuzzy control. Note that the driving section 92 may be controlled by providing a state feedback instead of directly feeding back the positional information. Particularly, the web guider 90 system may be controlled by an optimizing control method. In order to provide a state feedback, a state observer may be used to estimate the state. The state observer may be a filter such as a Kalman filter.

The contact section 91 can change the tension on the web W by contacting the surface W3 and/or W4 of the web W in the folding section 40. Possible shapes of the contact section 91 include a cone, a polyhedron such as a rectangular parallelepiped, a sphere, etc. In order to effectively correct the path of the web W, the contact section 91 is preferably a rotatable roller. The use of a rotatable roller allows for a reduction in the deviation of variations in the tension on the web W.

An example of a specific structure of the web guider 90 will be described.

The contact section 91 includes at least one roller 91. The roller 91 is revolvable on a central shaft 91c. One end of the central shaft 91c of the roller 91 is attached to a frame 94 so that the roller 91 is rotatable about the center of rotation O1 with respect to the frame 94. The other end of the central shaft 91c of the roller 91 is rotatably attached to one end O2 of the expansion/contraction section 93. By expanding/contracting the expansion/contraction section 93, the orientation of the roller 91, i.e., the inclination angle (orientation) of the roller 91 as viewed from the side, changes.

The roller 91 contacts the surface of the web W and is revolvable. When at least one of the inclination angle (orientation) and the position of the roller 91 is altered while the roller 91 is in contact with the surface of the web W, the alteration changes the dynamic friction force between the roller 91 and the web W, thereby varying the external force acting upon the web W. Thus, it is possible to alter the path of the web W.

The material of the roller 91 may be a metal, such as iron or aluminum, or a carbon graphite. In order to increase the friction force, at least the surface of the roller 91 is preferably made of a material providing a larger friction force with the web W than a metal or a carbon graphite, e.g., rubber, cork, or the like. Alternatively, a metal or a carbon graphite having an increased surface roughness, which provides a large friction with the web W, can be used as a material of the surface of the roller 91. In order to increase the surface roughness, the surface of the roller 91 may be subjected to a process such as painting or etching.

Basically, the web W is continuously carried (moved) in a direction Y perpendicular to the axis of the roller 91. In other words, the web W is carried (moved) in the tangential direction of the rotation of the roller 91 at the contact line (point) between the roller 91 and the web W. For example, in a case where an upper portion 91a of the roller 91 is located downstream of a lower portion 91b thereof, the side edge W1 or W2 of the web W near the roller 91 is displaced toward the lower portion 91b so that the running direction Y of the web W is perpendicular to the axis of the roller 91. In a case where the upper portion 91a of the roller 91 is located upstream of the lower portion 91b thereof, the side edge W1 or W2 of the web W near the roller 91 is displaced toward the upper portion 91a so that the running direction Y of the web W is perpendicular to the axis of the roller 91.

Alternatively, the positions of the side edges W1 and W2 can be aligned with each other by changing the revolution speed of the roller 91. For example, in a case where the roller 91 is revolved by a motor, the rotation speed of the motor may be changed so as to change the state of contact between the roller 91 and the web W, thereby varying the tension on the web W.

Figure 4A:
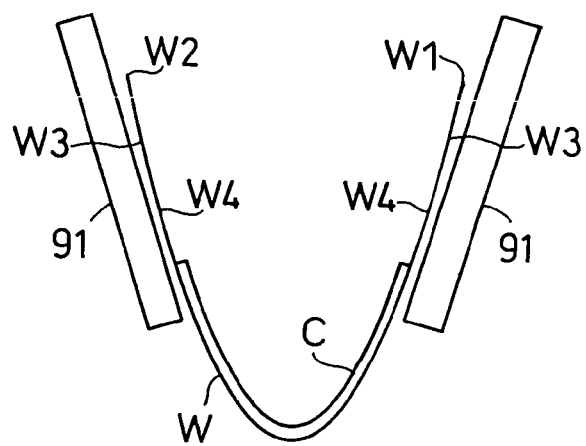
FIGS. 4(*a*), 4(*b*), 4(*c*) and 4(*d*) are transverse sectional views each showing a contact section.
Figure 4B:
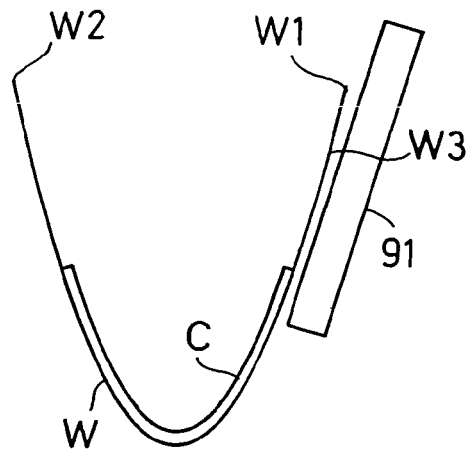
Figure 4C:
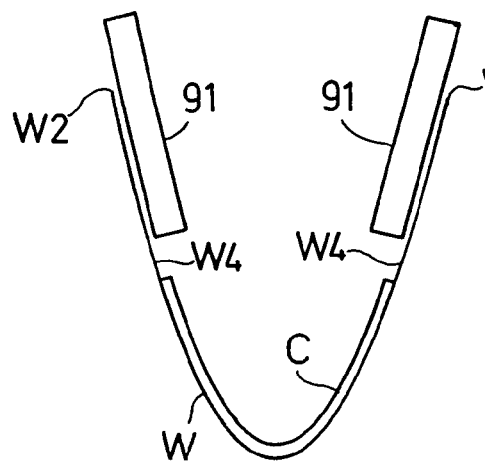
Figure 4D:
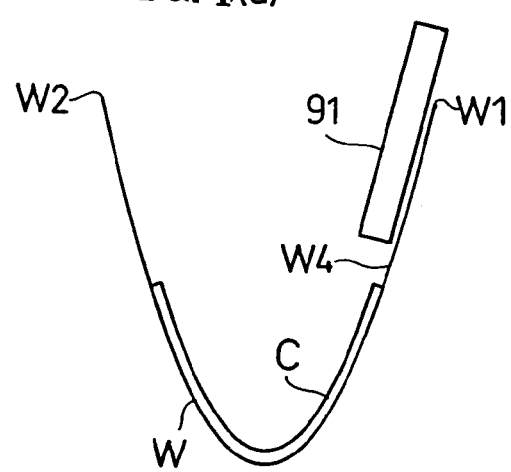

The structure of the web guider 90 is not limited to that shown in FIG. 4(a) as long as the tension on the web W can be changed. For example, as shown in FIG. 4(b), the contact section 91 may be provided for only one of the side edges W1 and W2 so as to contact one outer surface W3 of the web W. Alternatively, the contact section 91 may be provided for both of the side edges W1 and W2 or for only one of the side edges W1 and W2 so as to contact the inner surface W4 of the web W, as shown in FIG. 4(c) or 4(d).

Alternatively, at least two rollers 91 may be provided on each side as shown in FIGS. 5(a) and 5(b) so that the tension on the web W is changed by nipping the inner surface W4 and the outer surface W3 of the web W by the rollers 91, by winding the web W around two rollers 91, or by pressing two rollers 91 against the web W.

Moreover, in FIG. 3, a pair of first sensors 41 may be provided. In a case where a pair of first sensors 41 are provided, the control section 3 may correct the path of the web W as follows. First, the value of positional information from one of the first sensors 41 is subtracted from the value of positional information from the other first sensor 41 to obtain a subtraction value. Then, the subtraction value is squared to obtain a calculated value. The path of the web W can be corrected so as to bring the calculated value closer to a target value (e.g., "0").

Note that in addition to the action of the web guider 90, the folding sailor 1 may be movable in the width direction and in the vertical direction by the control section 3. Alternatively, the control section 3 may control both of the folding sailor 1 and the web guider 90.

Moreover, another web guider 100 for guiding the web W to the center of the folding sailor 1 may be provided upstream of the folding section 40 so that the center of the web W is guided to the center of the folding sailor (the abutting member) i.e., the center of the folding section 40. The web guider 100 includes another contact section 101 contacting the web W, and another driving section 102 for driving the contact section 101. The second sensor 103 is provided upstream or downstream of the other web guider 100 for detecting a positional misalign (displacement) of the web W and outputting the obtained information to the control section 3. The control section 3 controls the driving section 102 based on the information.

INDUSTRIAL APPLICABILITY

The present invention can be used, for example, for folding a web used in a worn article, etc.

The invention claimed is:

1. A folding apparatus, comprising:
a folding section for folding a web in two so that opposite side edges of the web are in a predetermined positional relationship with respect to each other;
a correction section including at least one roller for correcting a moving direction of the web by contacting the web in the folding section;
a detecting section for detecting a reference portion of the web to be used as a reference in a web folding operation so as to output positional information regarding a position of the detected reference portion; and
a control section for controlling at least one of an inclination angle or a revolution speed of the roller in the correction section and while the roller is in contact with the web based on the positional information so as to bring a positional relationship between the opposite side edges of the web closer to the predetermined positional relationship.

2. A folding apparatus according to claim 1, wherein the correction section corrects a moving direction of the web by altering a tension of the web.

3. A folding apparatus for folding in two a continuous web being continuous in a running direction of the web so that opposite side edges of the web are in a predetermined positional relationship with respect to each other, the apparatus comprising:
an abutting member provided so as to extend in the running direction between the opposite side edges of the web, wherein the abutting member abuts against the web to fold the web into a V or U shape;
a nipping member provided downstream of the abutting member for nipping the web folded by the abutting member so as to fold the web in two;
a contact section provided between an upstream end of the abutting member and the nipping member, the contact section including at least one roller for contacting an inner surface and/or an outer surface of the web being folded in the V or U shape;

a detecting section for detecting a reference portion of the web to be used as a reference in a web folding operation so as to output positional information regarding a position of the detected reference portion;

a driving section for changing a state of contact of the roller in the contact section and/or the abutting member with the web; and a control section for controlling an action of the driving section based on the positional information by controlling at least one of an inclination angle or a revolution speed of the roller in the correction section while the roller is in contact with the web so as to bring a positional relationship between the opposite side edges of the web closer to the predetermined positional relationship.

4. A method for producing a worn article, the method comprising the steps of:

placing an absorbent body on a surface of a web;

folding the web in two in a folding section so that opposite side edges of the web are close to or aligned with each other;

detecting a reference portion of the web to be used as a reference in a folding operation to generate positional information regarding a position of the detected reference portion;

correcting a path of the web based on the positional information so that the opposite side edges of the folded web are in a predetermined positional relationship with respect to each other by bringing a contact section into contact with the web in the folding section, wherein the contact section includes at least one roller in contact with the web and a control section for controlling at least one of an inclination angle or revolution speed of the at least on roller while the roller is in contact with the web;

bonding portions of the folded web to each other to form a bonded portion; and cutting the bonded web along the bonded portion.

5. A method for producing a worn article according to claim 4, further comprising the steps of:

placing an elastic member on a surface of the web; and forming a hole to be a leg hole in the web.

6. A folding apparatus comprising:

an abutting member extending in a running direction between opposite side edges of a continuous web, wherein the abutting member abuts against the web to fold the web into a V or U shape;

a nipping member downstream of the abutting member for nipping the web folded by the abutting member so as to fold the web in two;

a contact section between an upstream end of the abutting member and the nipping member for contacting an inner surface and/or an outer surface of the web being folded in the V or U shape; and a detecting section for detecting a reference portion of the web to be used as a reference in a web folding operation so as to output positional information regarding a position of the detected reference portion, wherein the folding apparatus controls an action of the contact section based on the positional information so as to bring a positional relationship between the opposite side edges of the web closer to a predetermined positional relationship, wherein the contact section comprises a roller extending in a direction of an axis along a width direction of the web folded by the abutting member, a driving section that changes an inclination angle of the axis of the roller with respect to the running direction of the web while the roller contacts the web folded in the V or U shape, each of the opposite side edges of the web spaced apart from each other, and a control section that brings the positional relationship between the opposite side edges of the web closer to the predetermined positional relationship by changing an external force transmitted from the roller to the web and that controls the drive of the driving section based on the positional information outputted from the detecting section.

7. A folding apparatus according to claim 6, wherein the contact section comprises a first roller and a second roller, wherein the first roller and the second roller contact a first and a second side surface of the web, standing face to face to each other, folded in the V or U shape by the abutting member.

8. A folding apparatus according to claim 7, wherein the first roller and the second roller are positioned along the first and second side surface of the web folded in the V or U shape by the abutting member such that the first roller and the second roller are closer together at a center of the web and further apart at the opposite side edges of the web.

9. A method for producing a worn article, the method comprising the steps of:

placing an absorbent body on a surface of a continuous web along a running direction of the web;

folding the web in two in a folding section so that opposite side edges of the web are close to or aligned with each other;

detecting a reference portion of the web to be used as a reference in a folding operation to generate positional information regarding a position of the detected reference portion;

correcting a path of the web based on the positional information so that the opposite side edges of the folded web are in a predetermined positional relationship with respect to each other by bringing a contact section into contact with the web in the folding section;

bonding portions of the folded web to each other to form a bonded portion; and cutting the bonded web along the bonded portion, wherein the contact section uses a roller extending in a direction of an axis along a width direction of the web folded by the abutting member, and a driving section for changing an orientation of the roller so as to change an inclination angle of the axis of the roller with respect to the running direction of the web while the roller contacts the web folded in the V or U shape, spaced apart from each of the opposite side edges of the web, thereby correcting a path of the web based on the positional information so that the opposite side edges of the folded web are in the predetermined positional relationship with respect to each other by changing an external force transmitted from the roller to the web.

10. A method for producing a worn article according to claim 9, further comprising the steps of:

placing an elastic member on a surface of the web; and forming a hole to be a leg hole in the web.

* * * * *